(12) United States Patent
Shiota

(10) Patent No.: US 7,094,294 B2
(45) Date of Patent: Aug. 22, 2006

(54) PROCESS FOR PRODUCING A MEDICAL GUIDE WIRE

(75) Inventor: Hiroyuki Shiota, Takarazuka (JP)

(73) Assignee: Nippon Cable System Inc., (JP)

(*) Notice: Subject to any disclaimer, the term of this patent is extended or adjusted under 35 U.S.C. 154(b) by 203 days.

(21) Appl. No.: 10/704,662

(22) Filed: Nov. 12, 2003

(65) Prior Publication Data

US 2004/0129352 A1 Jul. 8, 2004

(30) Foreign Application Priority Data

Nov. 13, 2002 (JP) ............................ 2002/330066
Oct. 9, 2003 (JP) ............................ 2003/351304

(51) Int. Cl.
*C21D 8/06* (2006.01)
(52) U.S. Cl. .................... 148/516; 148/519; 148/527
(58) Field of Classification Search ............ 148/516, 148/519, 527
See application file for complete search history.

(56) References Cited

U.S. PATENT DOCUMENTS

| 3,452,742 A | 7/1969 | Muller |
| 5,143,085 A | 9/1992 | Wilson |
| 6,139,540 A | 10/2000 | Rost et al. |
| 6,165,292 A | 12/2000 | Abrams et al. |
| 6,371,928 B1 * | 4/2002 | Mcfann et al. .............. 600/585 |
| 6,907,298 B1 * | 6/2005 | Smits et al. ................. 607/125 |
| 2004/0167442 A1 * | 8/2004 | Shireman et al. ........... 600/585 |

FOREIGN PATENT DOCUMENTS

| JP | 04-108456 A1 | 4/1992 |
| JP | 07-255856 | * 10/1995 |
| JP | 3300155 B1 | 4/2002 |
| WO | WO-01/26725 A1 | 4/2001 |

OTHER PUBLICATIONS

European Search Report for co-pending application EP 03 25 7120 completed on Mar. 3, 2004.
European Search Report, Application No.: 03 257 120.0-1526, Reference No. DB/NIP-03499/BP, dated Nov. 17, 2005.

* cited by examiner

Primary Examiner—George Wyszomierski
(74) Attorney, Agent, or Firm—Rader, Fishman & Grauer PLLC

(57) ABSTRACT

A process for producing a medical guide wire comprising a step S2, S5 for inserting the core wire and coil into a tubular die having the desired curved form, a step S3, S6 for heat-treating the core wire and coil in the die, a step 7 for removing oxide skin or films from the heat-treated core wire, a step S8 for assembling the obtained coil to the core wire, a step S9 for brazing or soldering an end of the coil to the core wire, a step S10 for grinding or sandering the obtained guide wire, and then a step for washing the guide wire.

13 Claims, 13 Drawing Sheets

(a)

(b)

PROCESS FOR PRODUCING A MEDICAL GUIDE WIRE

FIELD OF INVENTION

The present invention relates to a process for producing a medical guide wire specially to a guide wire having a curved or pig-tailed tip end be used for guiding a catheter.

BACKGROUND OF INVENTION

[Prior Art]
[Patent Reference 1] Japanese Unexamined Patent Publication No. 108456/1992A (Tokkai-hei 4-108456)
[Patent Reference 2] Japanese Patent publication No.3300155 B A guide wire is generally inserted into a blood vessel proceeding catheter in order to guide the catheter to a target point. And the tip is formed into a J-shape or loop-shape so that the tip can be inserted smoothly into the blood vessel which might wind hard. Such a guide wire has a core tapered toward the tip end, and a coil attached on the core wire whole or at the tip end potion partially. The core wire has a suitable strength or rigidity so that the core wire can be remotely controlled from user's hand side, and has flexibility so as not to injury the vein or blood vessel.

A typical prior art of guide wire is shown in FIG. 11. The guide wire 100 has a core 101 made of stainless steel, carbon steel, Ti—Ni wire, and the like, and a coil 102 made of stainless steel, platinum, platinum alloy, tungsten, and the like, and has a flexible carved tip end 100a.

In the Patent reference 1, as shown in FIG. 12a there is described a process for producing a guide wire by curling the tip end 101a of a core 101 into J shape previously, curling the corresponding portion 102a coil (spring member) 102 into J-shape, and thereafter combining those members (see page 2, left upper column of the publication). Further, there is proposed another producing process, as shown in FIG. 12b, by curl-forming a coil into J-shape previously only and, then combining a straight coil 102.

In Patent Reference 1, it is stated that the former process is troublesome since curvature of the core 101 and coil 102 are not precisely accorded, and the latter process can not produce a guide wire with precisely curved shape. And Patent reference 1 proposes to form the coil 102 with a sparse portion in number of turns in a portion corresponding to the curved portion 101a of the core 101, with keeping the latter process basically. And by using the producing process, an elastic deformation of the J-shaped portion 101a due to the elastic force of the coil 102 can be controlled. As material of the core 101 and the coil 102, superelastic metal such as Ni—Ti alloy is mentioned other than stainless steel.

Besides, Patent Reference 2, as shown in FIG. 13 discloses a producing process by combining a straight core 101 and a straight coil 102 previously, inserting the combination 103 into a die 105 having J-shaped groove 104, attaching a lid 106 on the die, and performing heat-treatment to form a curved shape. In this producing process, the material of the core 101 is stainless steel or carbon steel, and the material of the coil 102 is stainless steel, platinum, platinum, gold or tungsten.

DISCLOSURE OF INVENTION

Problem to be Solved

In the producing process in Patent Reference 1, a core 101 is formed by curving a metal wire. However, such simple curving causes spring-back. Therefore, in order to obtain precisely a predetermined curvature, it is necessary to curve excessively so that the shape returned by spring-back becomes to the predetermined shape. Further, when a metal wire is curve-formed, internal stress remains which causes deformation after long term from the original shape.

The producing process of Patent Reference 2 has an advantage that no spring-back is caused since the core 101 and the coil 102 are combined and the heat-treatment is performed with keeping the predetermined shape by inserting the combined core 101 and the coil 102 into the die 105. Further, the internal stress is reduced by the heat-treatment. However, long time is required for heating and cooling of the die and product, since whole of die and product are heated.

In addition, in the producing process, a material with high melting point is necessary as a brazing or soldering material. Therefore, the brazing or soldering step becomes troublesome. That is to say, in a general type guide wire, as end of the coil 102 is jointed to the core 101 when the core 101 and coil 102 are assembled. In this case, though it is preferable to use a soft soldering material such as half and half solder which can melt at low temperature, such soft soldering material can not be used since it becomes 400–600° C. during the heat treatment. Therefore, it is necessary to use hard soldering material or brazing filler metal, for example, with 600° C. or higher in melting point. Therefore, the brazing or soldering step is troublesome.

The object of the present invention is to provide a process for producing a guide wire which can accord the curvature shape to the designed shape as precisely as possible, and which can make shorter the time of production. Further, another object of the present invention is to provide a producing process which can accord the curvature shape to the designed shape as precisely as possible, and in which soldering or brazing or soldering material can be selected as freely as possible.

Means to Solve the Problem

The first aspect of the producing process of this invention for a medical guide wire comprising a core wire and a coil attached on the periphery of the core wire is characterized in that the core wire and the coil are heat-treated to shape a desired curved form using each separate die, and then the shaped coil is attached to the periphery of the shaped core wire.

A process for producing such medical guide wire is preferable to be so carried out that the core wire and/or the coil are inserted into the tubular die having the desired curved form and then heat-treated. Further, it is preferable to be so carried out that the core wire and/or the coil are inserted into a die having a guide groove of desired curved form. Furthermore, it is preferable to be so carried that the coil is wound around the periphery of a rod die having a desired outer diameter and then heat-treated.

The second aspect of the producing process of this invention for a medical guide wire comprising a core wire and a coil attached on the periphery of the core wire is characterized in that the coil is attached to the periphery of the core wire, and that both of them are inserted into a tubular die having a desired form in order to be heat-treated.

The third aspect of the producing process of this invention for a medical guide wire comprising a core wire, a coil attached to the periphery of the core wire, and a flat strip plate located inside of the coil is characterized in that the process has following three steps; a first step wherein the flat strip plate is inserted into the coil and an end of the plate is fixed to an end of the coil; a second step wherein the core wire previously heat-treated to shape a desired curved form is inserted into the coil obtained in the first step; and a third step wherein at another end of the coil obtained in the second step, the core wire, the coil, and the flat strip plate are fixed to the core wire after the position of the coil being adjusted to the core wire.

In these producing processes, it is preferable that the heat-treatment is comprised of a 3~200 minutes heating step at the temperature of 80~700° C. and a succeeding heat release step.

Effect of Invention

In the first aspect of the producing process of this invention, since the heat-treatment of the core wire and the coil are carried out separately, the temperature and the heating time adaptable to the each material and the shape can be set minutely. Attaching the coil to the periphery of the core wire after the heat-treatment allows employment of low-melting soft brazing or soldering material such as solder, thereby facilitating easy brazing or soldering, accompanying no heat damage to the base metal.

In the case that the core wire and/or the coil are inserted into a tubular die having the desired curved form and then heat-treated, since the heat-treatment is carried out in the tubular die, the heating time and the cooling time are shortened to reduce the producing time. In the case that the core wire and/or the coil are inserted into a die having the desired form of a guide groove and then heat-treated, since the core wire and the coil is inserted into each separate die having a desired guide groove and the coil is attached to the periphery of the core wire afterward, low-melting soft brazing or soldering material such as solder can be employed, thereby facilitating easy brazing or soldering.

In the case that the coil is wound around the periphery of a rod die having a desired outer diameter and then heat-treated, since the coil is exposed to outside, the heat-treatment time can be significantly reduced. Further, since plural coils can be wound around the periphery of the rod die, simultaneous heat-treatment of plural coils with one rod die can be carried out. After the heat-treatment, the coils are cut one by one obtaining each heat-treated coil efficiently.

In the second aspect of the producing process of this invention, since the coil is attached to the periphery of the core wire, and both of them are inserted into a tubular die having a desired form and then heat-treated, the heating time and the cooling time can be shortened to reduce the producing time. Further, in the case that the coil is previously attached to the periphery of the core wire and the end of the coil is brazed or soldered to the core wire, since the brazed or soldered part is located near the end of the tubular die, the temperature of the brazed or soldered part can be reduced allowing the use of relatively low melting brazing or soldering material.

In the third aspect of the producing process of this invention, a medical guide wire comprising a core wire, a coil attached to the periphery of the core wire, and a flat strip plate located inside of the coil, the producing process has following three steps; a first step wherein the flat strip plate is inserted into the coil and an end of the plate is fixed to an end of the coil; a second step wherein the core wire previously heat-treated to shape a desired curved form is inserted into the coil obtained in the first step; and a third step wherein at another end of the coil obtained in the second step, the core wire, the coil, and the flat strip plate are fixed to the core wire after the position of the coil being adjusted to the core wire. Employment of these three steps provides a core wire with reduced spring-back, and since the coil is fixed on the periphery of the core wire after adjustment of the position, high dimensional accuracy is achieved. Further, in the above producing process, when the heat-treatment is comprised of a 3~200 minutes heating step at the temperature of 80~700° C. and a succeeding heat release step, the removal work of oxide skin or films on the core wire and the coil done after the heat-treatment becomes easy.

DETAIL DESCRIPTION OF THE INVENTION

Figure 1:
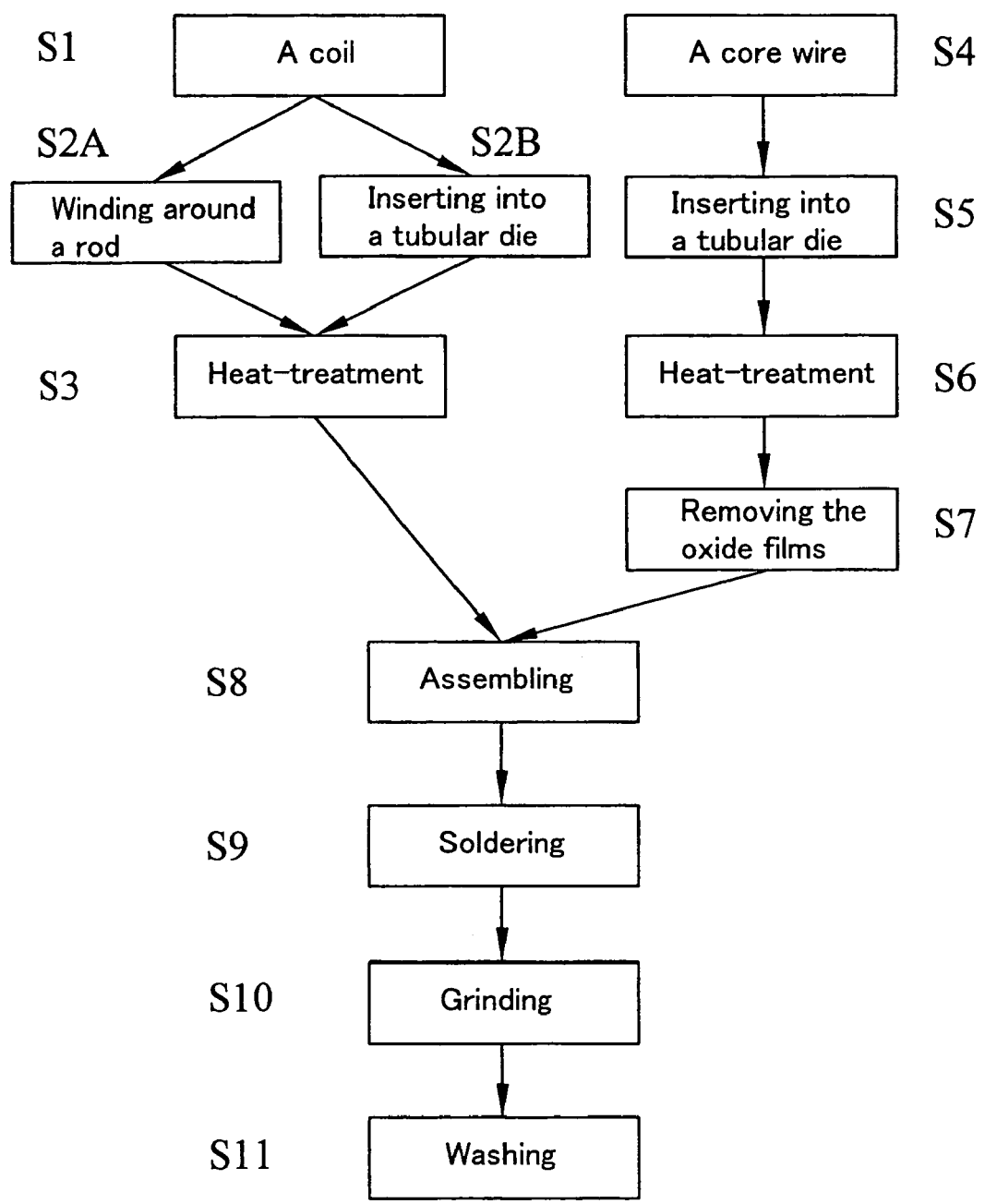
FIG. 1 is a flow chart showing an embodiment of the producing process of this invention.

The producing process shown in FIG. 1 comprises a step S1 for preparing a coil, a step S2A or S2B for attaching the coil to a die, a step S3 for heat-treating the coil in the die, a step S4 for preparing a core wire separately from the coil, a step S5 for inserting the core wire into a tubular die, a step S6 for heat-treating the core wire in the tubular die, a step 7 for removing oxide skin or films from the heat-treated core wire, a step S8 for assembling the obtained coil to the core wire, a step S9 for brazing or soldering an end of the coil to the core wire, a step S10 for grinding or sandering the obtained guide wire and a step S11 for washing the guide wire. In the step for attaching the coil, the coil can be wound around a rod bar or stick (step S2A), or the coil can be inserted into a tubular die (step S2B).

Figure 2:
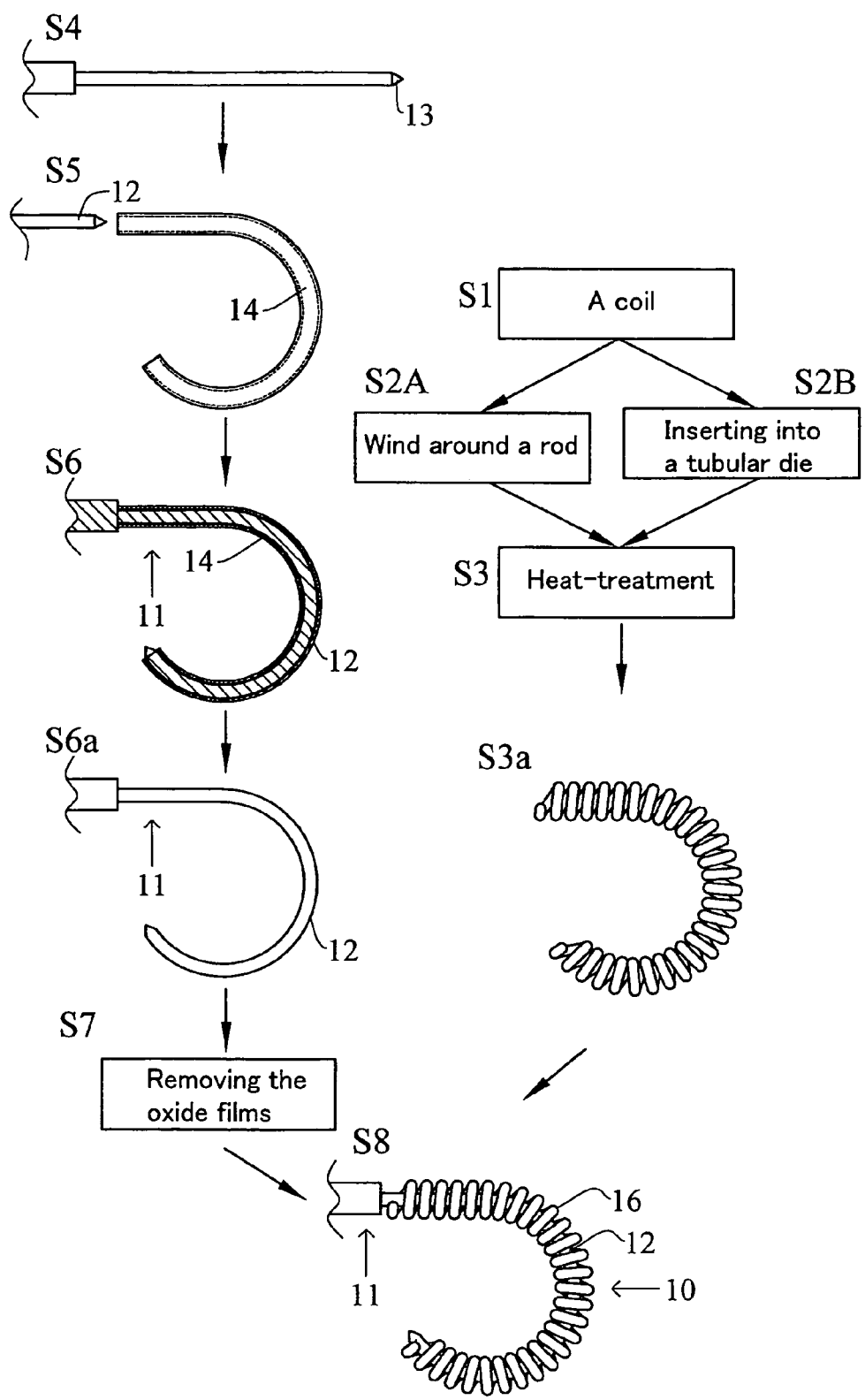
FIG. 2 is a process chart showing the detailed heat-treatment process of the core wire in the producing process of FIG. 1.

FIG. 2 shows the detail process of FIG. 1. At first, the step for preparing a core wire 11 shown at the left side of FIG. 2 is explained. To prepare the core wire 11, a wire of metal, such as stainless or carbon steel of 0.3–1.0 mm in diameter is cut to a predetermined length of 3000 mm or less. Then, the metal wire is formed to a predetermined shape with predetermined accuracy (S4). For example, a portion to be curved is reduced in diameter (herein after, the portion is stated as reduced portion 12), a tip end is formed in a tapered shape, and a bottom end is ground. The process to reduce partially can be performed by known process, such as drawing through a die. As a material of the core wire, Ni—Ti wire and the like can be used in addition to the above mentioned.

Next, the reduced portion 12 of the obtained core wire 11 is inserted in a curved or bent tubular die made of thin metal (S5). The reduced portion 12 can be wound around a cylindrical rod (not shown in the drawing). In FIG. 2, the reduced portion of the core wire 11 is formed in a J-like shape, and the number of winding is less than one. However, the number of winding can be one and half or more. In such case, the reduced portion 12 is shape-formed by using a helical tubular die (see FIG. 4). When the reduced portion 12 of the core wire 11 is wound around a rod, the shape-forming with winding number over one is easy. The material of the tubular die 14 and the rod is preferably made of metal with high thermal conductivity and high formability. For example, stainless steel and copper alloy can be used as the material. The inner diameter of the tubular die 14 is preferably 3.0 mm or less on the view point of the heating and cooling or heat radiation in short time. The shape of curvature of the tubular die 14 is formed to the predetermined shape of core wire 11, or made slightly small shape in the view point of return back of the core wire 11 after the forming. Since the reduced portion 12 of the core wire 11 has elasticity, relatively easy to insert the reduced portion 12 into the curved tubular die 14.

Then the core wire 11 is put in a furnace together with the tubular die 14 in order to be heat-treated in the air or in the atmosphere of inactive gas or inert gas (S6). As the inactive gas or inert gas, Nitrogen, Helium, Argon, Argon mixed gas etc. are used, where Argon is preferable. The temperature and the time of the heat-treatment is preferable to be 80~700° C. and 3~200 minutes respectively.

After heat releasing, the core wire 11 is extracted from the tubular die 14 (S6a in FIG. 2), thereby the reduced portion 12 of the core wire 11 is shaped into a curved form. In this condition, almost of the internal stress is removed to maintain its shape for a long time, and it recovers original shape when elastically deformed. Further, the oxide skin or films of the obtained core wire 11 having a desired curved are removed (S7).

Figure 3:
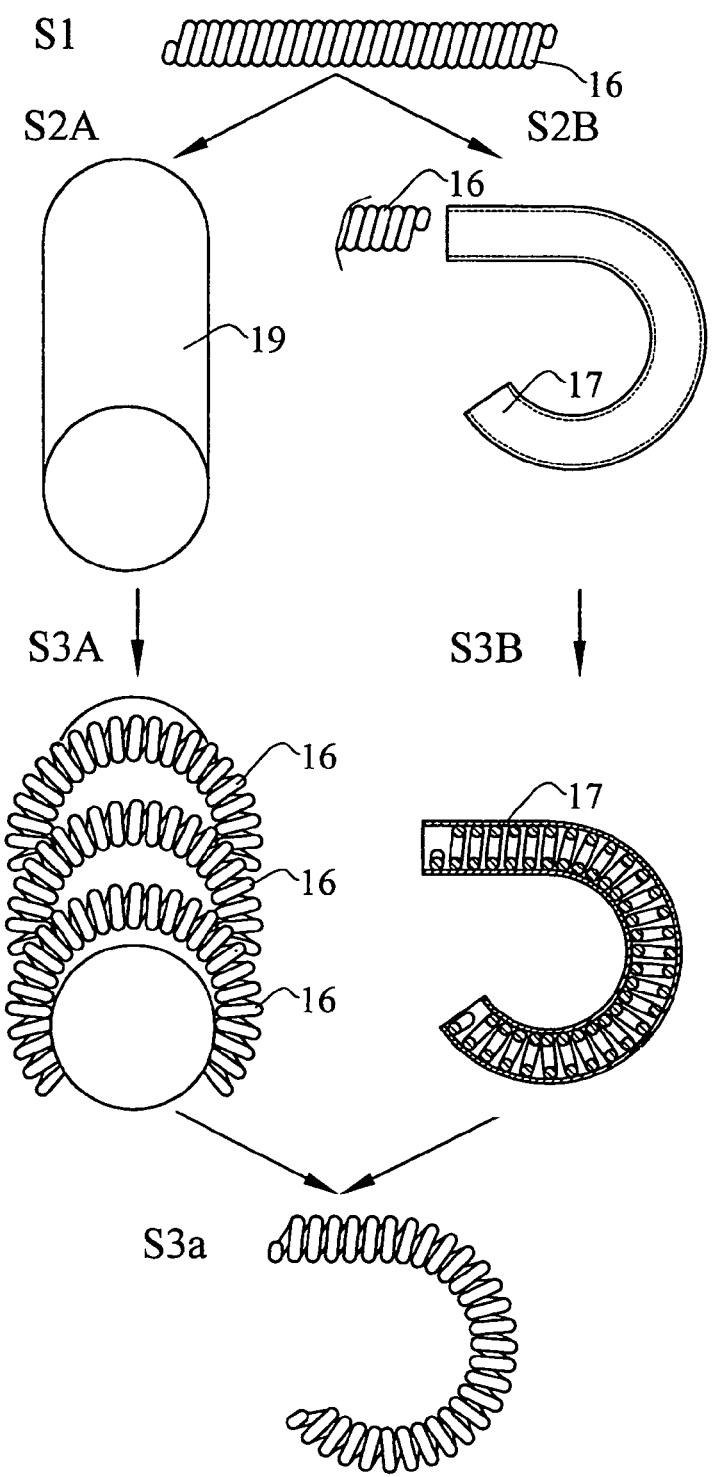
FIG. 3 is a process chart showing the detailed heat-treatment process in the producing process of FIG. 1.

The producing process of the coil 16 is described bellow (S1) with reference to FIG. 3. As the coil 16, a metal wire such as spring steel wire made of stainless steel etc. having the diameter of 0.05–0.5 mm is used. For the material of the coil, in addition to described above, roentgenopaque platinum, platinum alloy, gold, tungsten, or those alloys can be employed.

Figure 4:
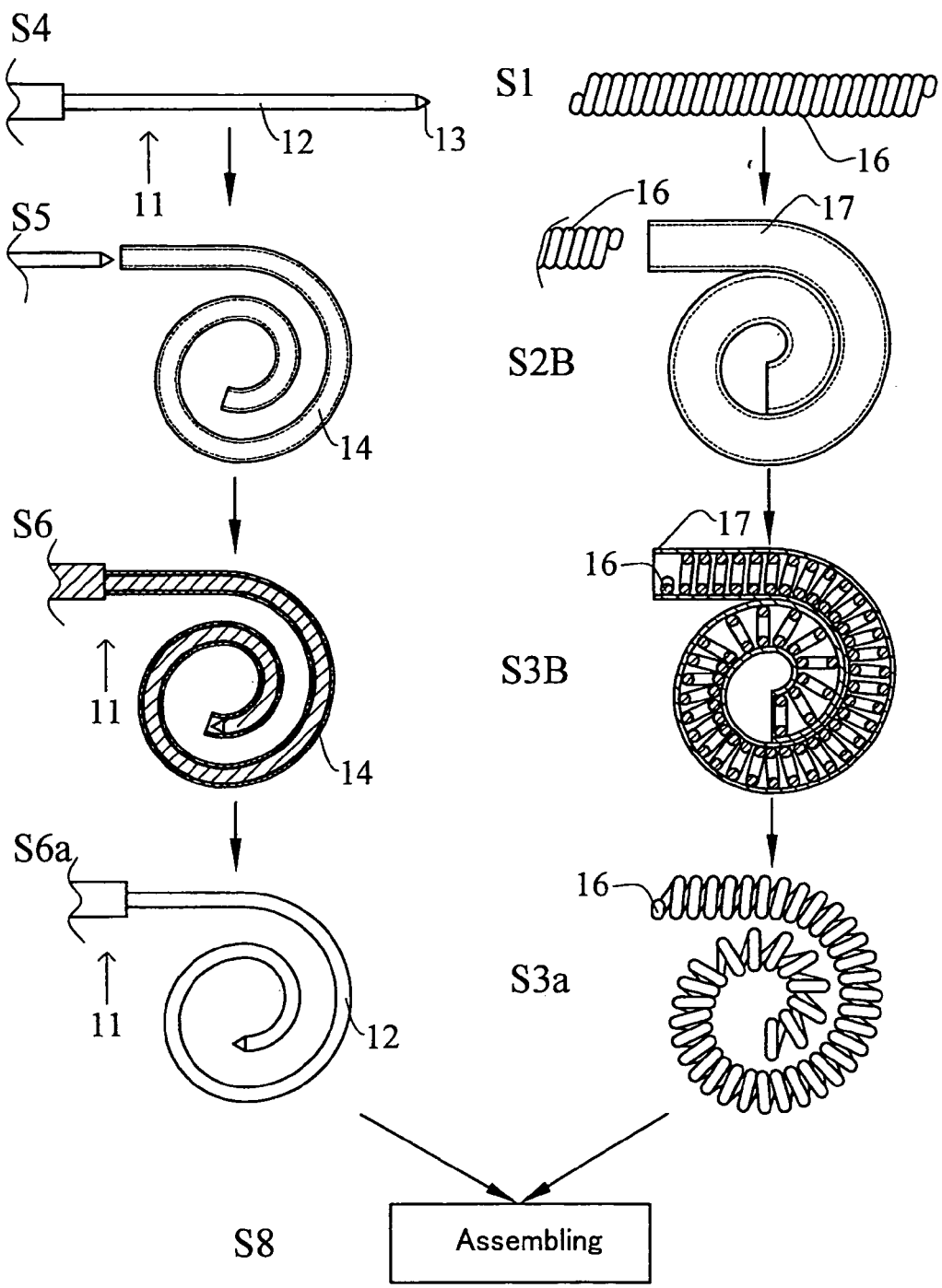
FIG. 4 is a process chart showing the other embodiment of the heat-treatment process of the core wire and the coil.

The coil 16 is attached to the outer surface of a cylindrical rod 19 (S2A) by winding, or inserted into the thin metal tubular die 17 (S2B) having curved form. In the case that the coil 16 is wound around the outer surface of the rod 19, plural of the coil 16 can be wound for one time heat-treatment (S3A). The coil 16 having enough length for plural coils can be wound several times for one time heat-treatment (not shown in the figure). As the rod 19 and the tubular die 17, those made of stainless, copper alloys can be used. The shape of curvature of the rod 19 and the tubular die 17 is formed to the predetermined shape of core wire 16, or made slightly small shape in the view point of return back of the core wire 16 after the forming. Since the coil 16 has elasticity, it can be wound around the outer surface of the rod 19 and inserted into the tubular die 17 easily, As shown in FIG. 3, the coil 16 is about J-shaped where the turn of coil 16 is less than one. However, as shown in FIG. 4, it can be one and half turn or more like the core wire 11. In this case, the core wire 11 is shaped using a spiral tubular die.

And then, like the core wire 11, the coil 16 is put in a furnace together with the rod 19 or the tubular die 17 and heat-treated in the air or in the atmosphere of inactive gas or inert gas ($S_3$). The temperature and the time of the heat-treatment is preferable to be 80~700° C. and 3~200 minutes respectively. After heat releasing, the coil 16 is extracted from the rod 19 or the tubular die 17. In the case that the coil 16 is wound around the rod 19 with its length equal to that of several coils, it is cut into every part having the length of one coil after being extracted, thereby the curved coil 16 is obtained (S3a in FIG. 3).

Next, as shown in step S8 in FIG. 2, the coil 16 is attached to the core wire 11 whose reduced portion 12 is curved. Soft brazing or soldering material such as solder is used for soldering material, thereby the guide wire 10 having the core wire 11 to which the coil 16 is attached is obtained.

After that, as shown in FIG. 1, the soldered end part and the front part are ground ($S_{10}$) and washed to complete the producing of the guide wire 10. Then, its dimension is inspected and packed.

In the producing process described above, since the heat-treatment is carried out with the core wire 11 and the coil 16 being inserted into the thin metal tubular die 14, 17 or being wound around the rod 19 with maintaining its shape, the heat in the furnace is easily transferred to the core wire 11 and the coil 16 allowing the fast rise in temperature up to a required temperature for the heat-treatment, the shorter heat releasing time, and the reduced producing time. Further, since the core wire 11 and the coil 16 are separately shaped and then brazed or soldered after assembled into one piece, the low-melting brazing or soldering material such as solder can be used facilitating easy soldering work. Additionally, the heat-treatment in the atmosphere of inactive gas or inert gas produces less oxide skin or films.

Figure 5:
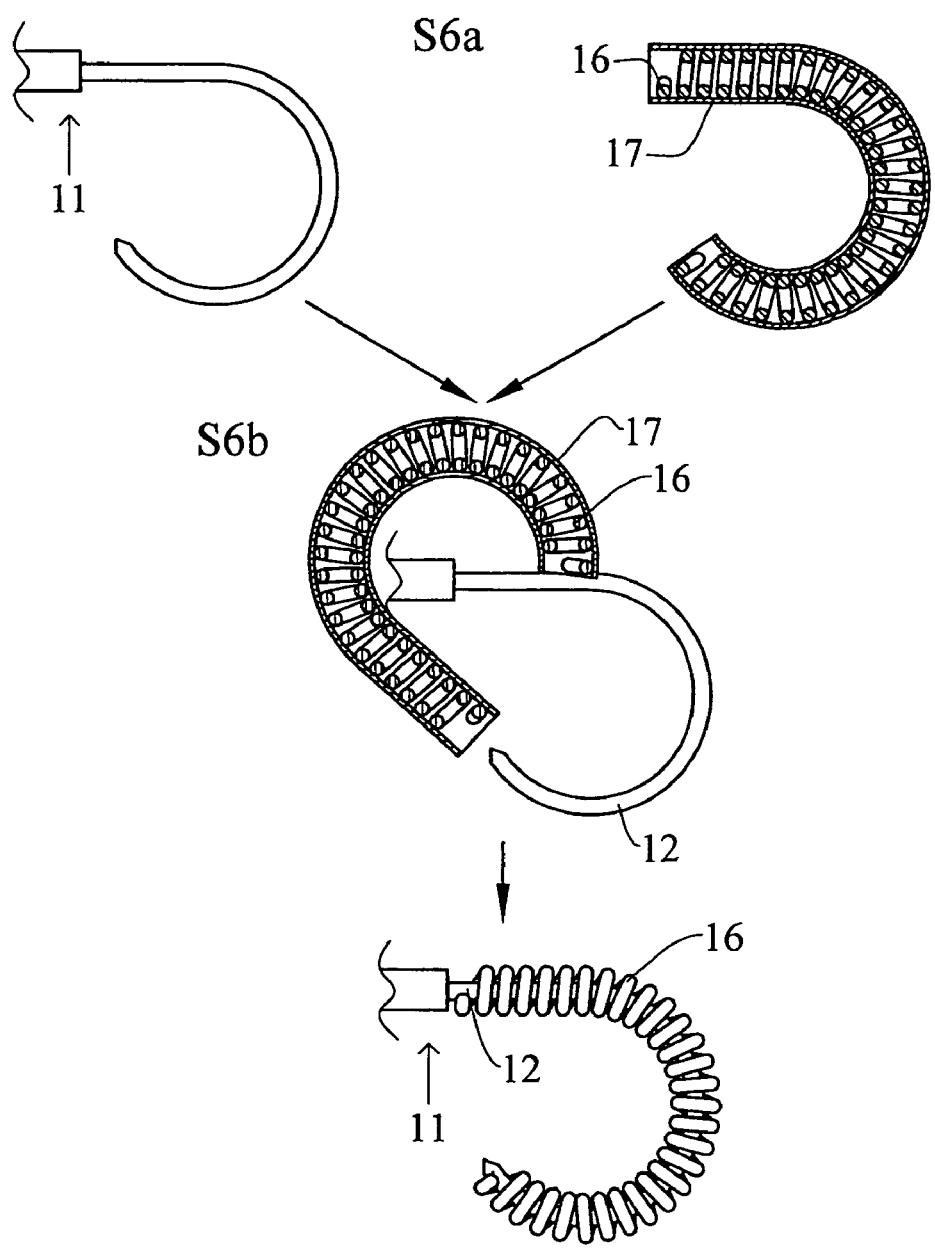
FIG. 5 is a partial process chart showing the other embodiment of this invention.

In the embodiment described above, after the heat-treatment of the coil 16, it is extracted from the tubular die 17 to attach to the core wire 11. However, as shown in FIG. 3, the core wire 11 can be inserted into the coil 16 without being extracted from the tubular die 17 (S6b in FIG. 5). In this case, the coil 16 can be handled as a rigid body, thereby allowing easier insertion of the core wire 11. After the insertion of the core wire 11, it is brazed or soldered after extracted or it is extracted after brazing or soldering.

Figure 6:
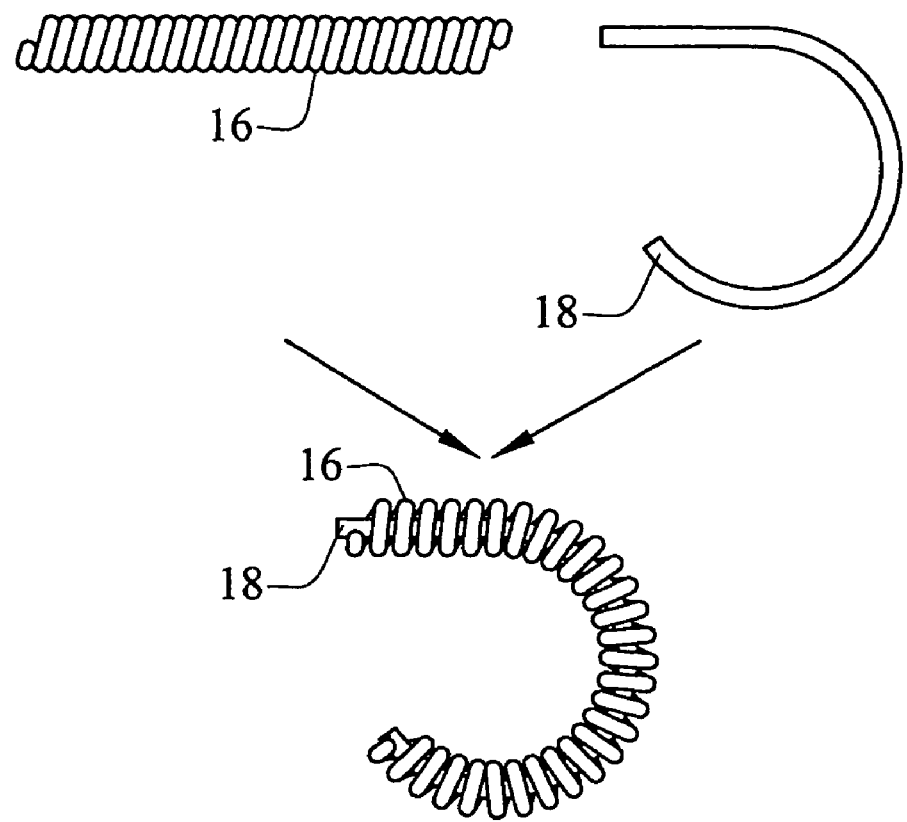
FIG. 6 is a partial process chart further showing the other embodiment of this invention.

In the embodiment shown in FIG. 2, the heat-treatment is carried out after the insertion of the coil 16 into the tubular die 17. However, as shown in FIG. 6, the heat-treatment can be carried out after the rod 18 is inserted into the center of the coil 16. As the rod 18, a heat-resistant and rigid rod is used. In this process, when the rod 18 is extracted from the coil 16, the core wire 11 can be inserted successively following the rod being extracted, thereby facilitating the easy insertion of the core wire 11.

Figure 7:
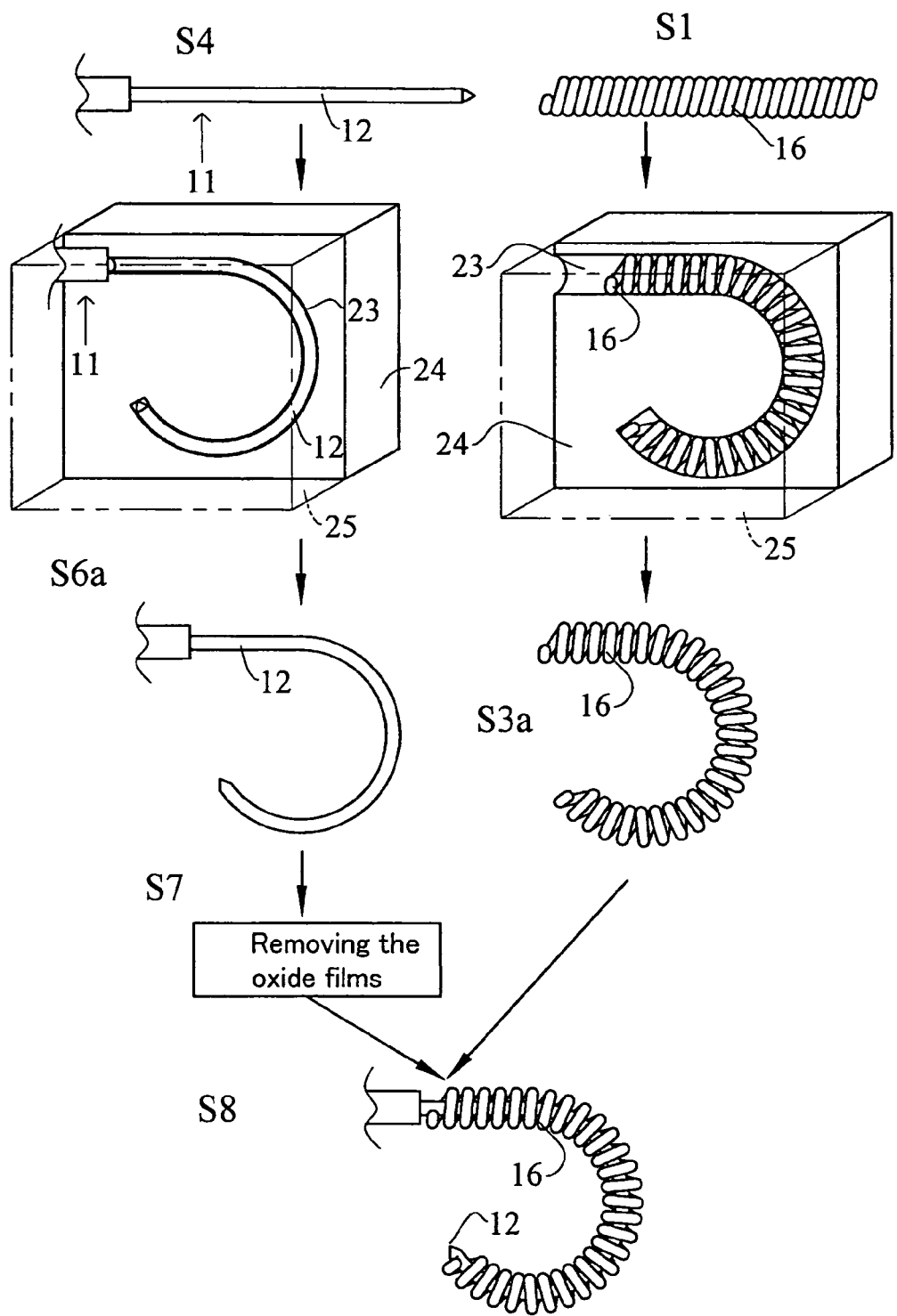
FIG. 7 is a process chart showing the other enbodiment of the producing process of this invention.

The producing process shown in FIG. 7 is same as that shown in FIG. 2 except for the use of the die 24 provided with the concave groove 23 for shaping like the Patent reference 2 and the use of the cap 25 to cover the die. This producing process needs the longer heating time in the heat-treatment and the longer heat releasing time. However, this process has about the same advantageous effect as that shown in FIG. 2 as follows; when the core wire 11 is brazed or soldered to the coil 16, low-melting brazing or soldering material such as solder can be used; the removal of the oxide skin or films after the heat-treatment is easy.

In any embodiment described above, the reduced portion 12 is formed at the front end of the core wire 11 and the coil 16 is attached to the periphery of the reduced portion 12. However, the coil can be attached to the whole length of the core wire 11. Further, the reduced portion, the coil and the curved part can be provided at one end of the core wire 11 together with the same parts, the reduced portion, the coil and the curved part, provided at the other end of the core wire. In this case, by changing the curvature, the length, or the center angle, it is preferable for the user to be able to choose which curved part is regarded to be the front end for inserting into a human body. Furthermore, In addition, the other end can be left straight with only the reduced portion and the coil being provided.

Figure 8:
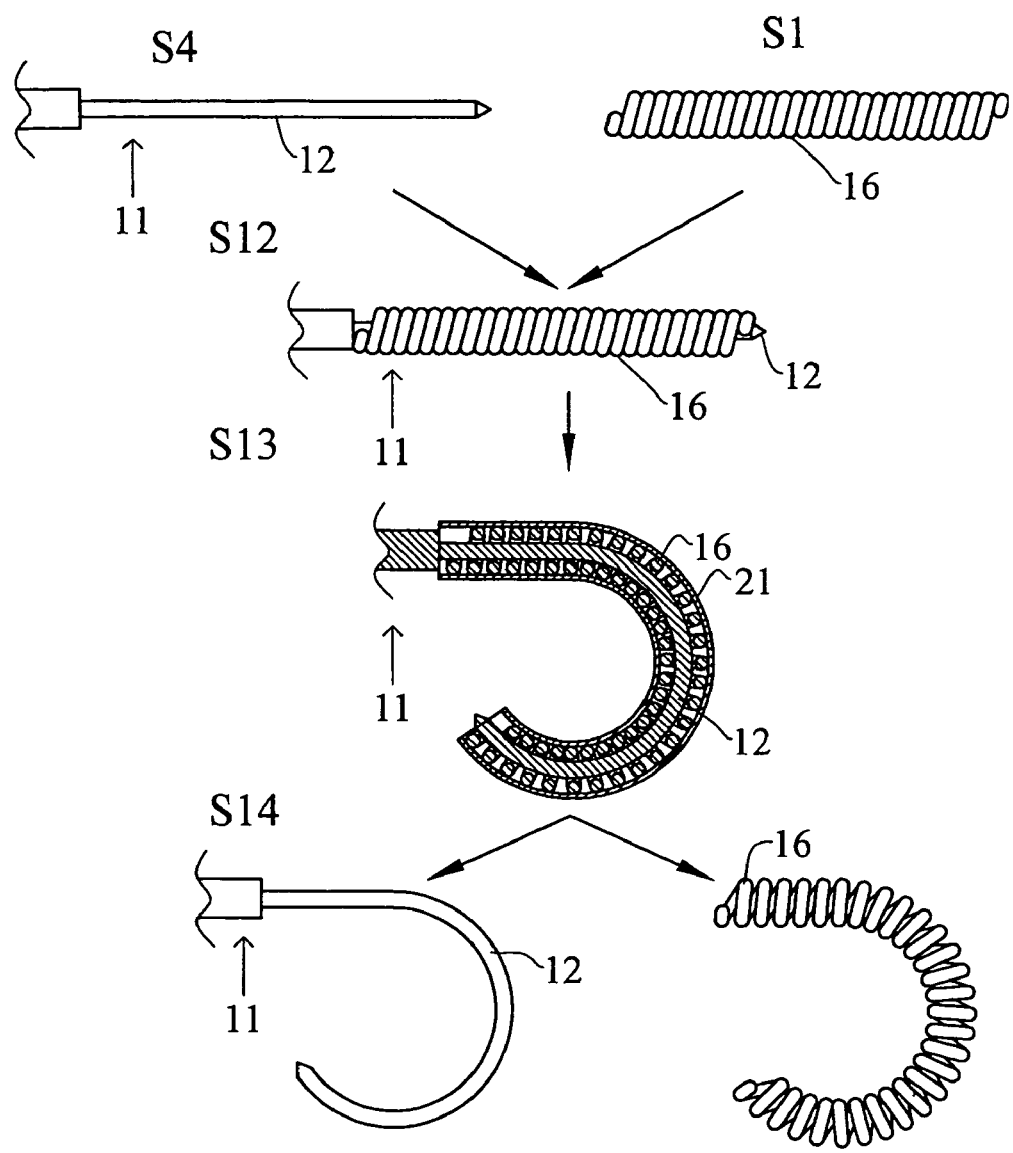
FIG. 8 is a process chart showing the second aspect of producing process of this invention.

The producing process shown in FIG. 8 is the same as that shown in FIG. 2 in the point that it uses the tubular die for shaping. However, it differs in the point that the core wire 11 and the coil 16 are assembled into one piece (step S12) in their straight shapes (step S1, S4), and both of them are inserted into the tubular die 21 and then heat-treated (step S13). After the heat-treatment, both of them are extracted from the tubular die 21, and once the coil 16 is removed from the core wire 11 (step S14). After that, as shown in latter step of FIG. 1, the oxide skin or films are removed from the core wire 11 (step S7 in FIG. 1) and reassembled into one piece (step S8), brazed or soldered (step S9), ground (step S10) and washed (step S11).

In this producing process, the heat-treatment process is simplified because only one common die 21 is necessary to be provided and they are both heat-treated at one time. However, it has intricacy in the producing process that the coil once assembled has to be removed after the heat-treatment. Regarding the producing quality, the accuracy is inferior to the case in FIG. 2, because the core wire 11 is elastically deformed in the coil 16. On the other hand, the producing process is the same as shown in FIG. 2 in the process of removing the oxide skin or films and brazing or soldering with low-melting material such as solder keeping the similar quality.

As well, the brazing or soldering can be done when they are assembled (S12), and after the heat-treatment, only the grinding and the washing are carried out. In this case, hard soldering material or brazing filler metal whose melting point is higher than the heat-treatment temperature is used, thereby causing the brazing or soldering process to be intricate. Further, the process of removing the oxide skin or films after the heat-treatment can not be done by a normal process due to the existence of brazing or soldering material for brazing or soldering, thereby causing the need of the intricate process. Furthermore, in that intricate process, there is a possibility of significant effect on the brazing or soldering material to be deteriorated in strength.

Figure 9:
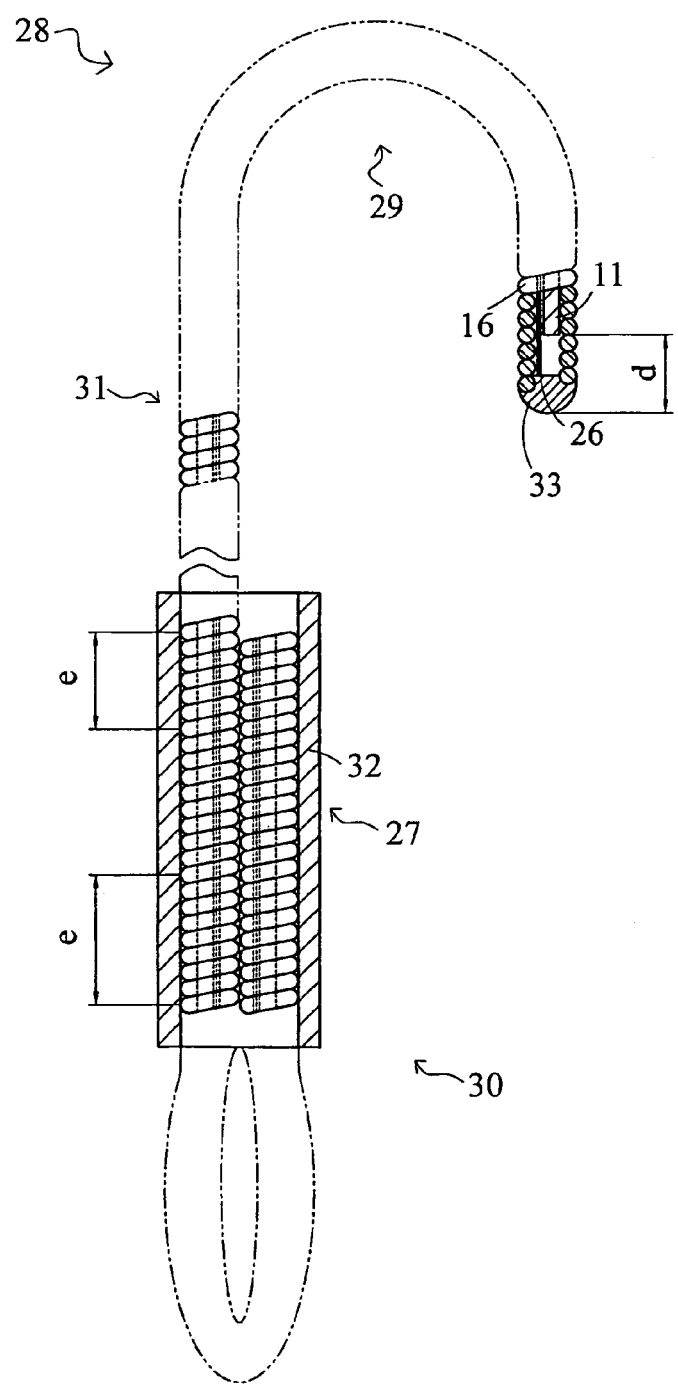
FIG. 9 is a drawing showing the third aspect of the producing process of this invention.

FIG. 9 shows the third aspect of this invention. This aspect is called stiletto used together or separately with the guide wire. The stiletto 28 is comprised of the core wire 11, and the coil 16 whose center part is inserted into the periphery of the core wire 11. The core wire 11 is comprised of the front end J-shaped part 29, a folded part 30 of the back end, and a body 31 in between these two parts. On the front end J-shaped part 29 of thus comprised stiletto 28, a spherical part 33 and a flat strip plate 26 which is fixed by the spherical part 33 at its one end and located inner surface of the coil 16 and inside of the curved are provided. The spherical part 33 fixes the coil 16 and the flat strip plate 26. The other end of the stiletto 28 comprises a folded part 30, and this part forms a handgrip 27. The outer surface of the handgrip 27 is wholly covered by a tube 32.

Next, the each component is described in detailed. Overlapping description with the previous embodiment is abbreviated. The core wire 11 is 0.3~1.0 mm in diameter and is a spring steel wire made of stainless steel etc, which is similar to the embodiments described above. The whole length of the wire is 500~1500 mm. The coil is 0.5~1.5 mm in diameter and is a spring steel wire similar to the above embodiments. The whole length of the coil is 500~1500 mm and preferably 1100 mm.

The flat strip plate 26 is a wire such as rolled wire 0.02~0.5 mm in thickness, 0.1~0.5 mm in width and is made of stainless steel same as the coil. For the assembling of the coil 16 and the flat strip plate 26, the low-melting soft brazing or soldering material such as solder can be used. However, employment of plasma welding etc. having strong thermal concentration allows fast welding work, small welding distortion, and higher dimensional accuracy. With the spherical part 33 thus formed by welding, the coil 16 and the flat strip plate 26 whose one end is attached to the front end of the coil 16 is fixed by welding. Because the flat strip plate 26 has relative flexibility in the direction of the thickness, the coil 16 becomes bendable in the same direction and has rigidity in axial direction, thereby achieving high axial buckling strength with respect to high flexibility and featuring ease of use.

The handgrip 27 is formed by welding the mated part each other which is made by folding at the folded part 30 using solder etc. To grip the handgrip 27 enables easy operation of the stiletto 28. The handgrip 27 is covered with a resin tube 32 serving to prevent from slippage and to improve the feeling of operation. The material of the tube 32 made of resin is preferable to be vinyl chloride or urethane.

Figure 10:
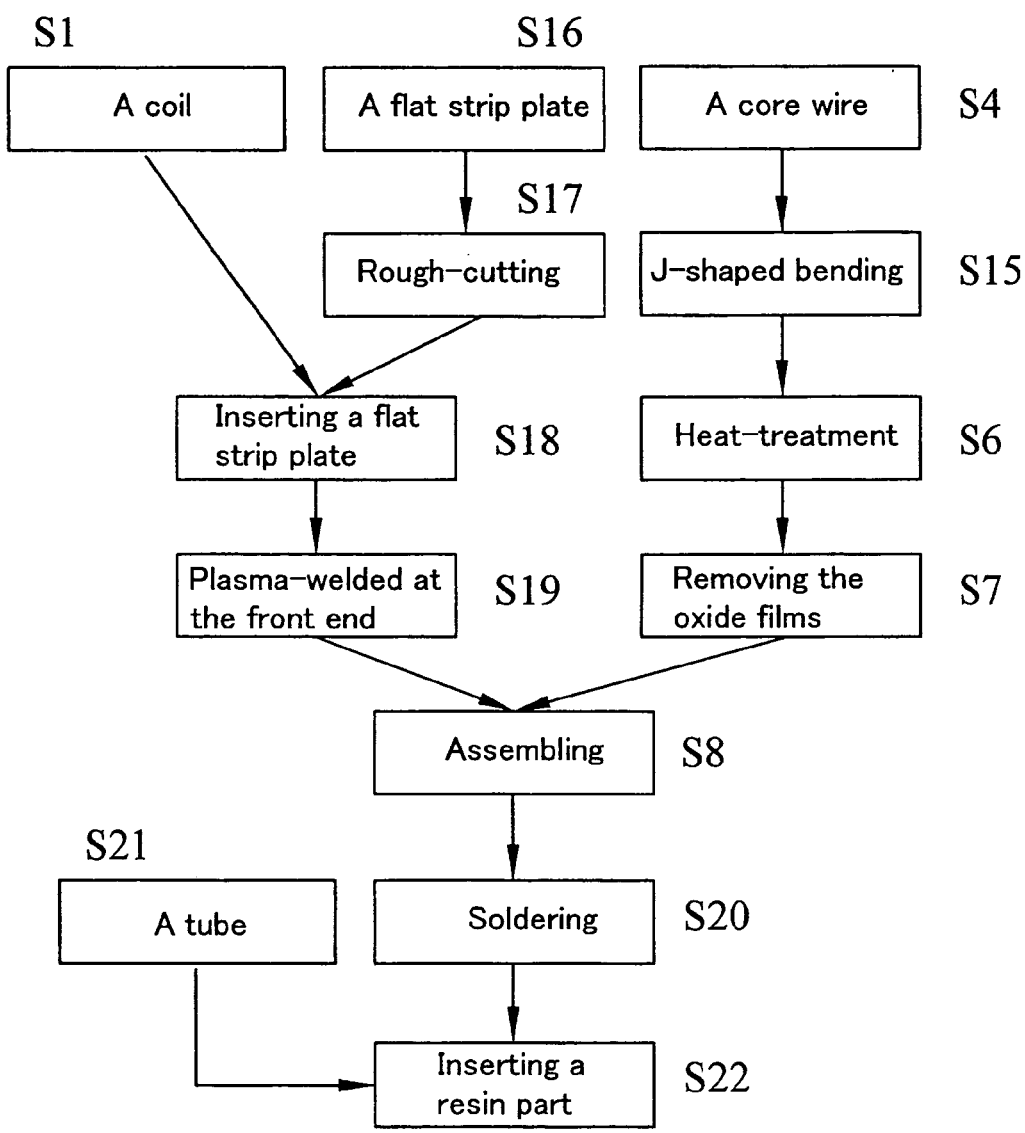
FIG. 10 is a process chart showing the third aspect of the producing process of this invention.
Figure 11:
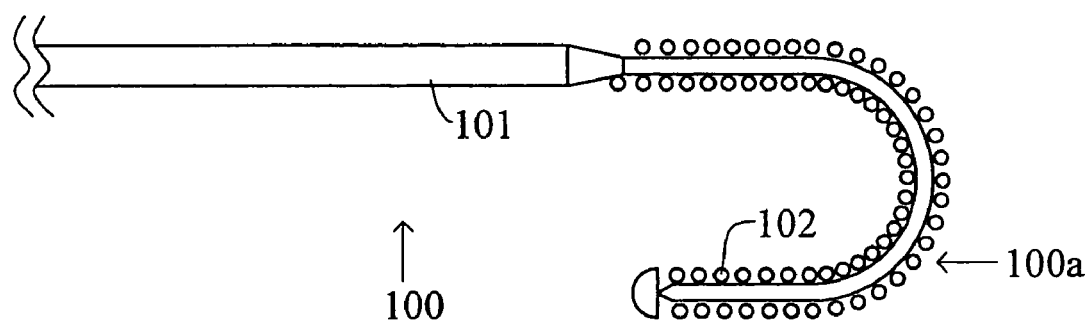
FIG. 11 is an outline front view showing an example of the guide wire produced by the producing process of this invention.
Figure 12:
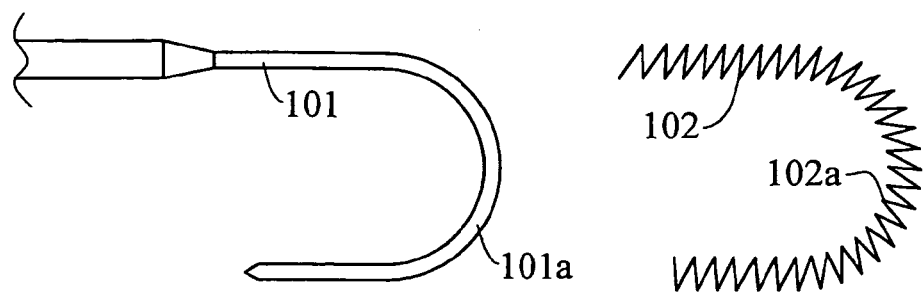
FIG. 12a and FIG. 12b are process charts showing an example of the conventional producing process respectively.
Figure 12:
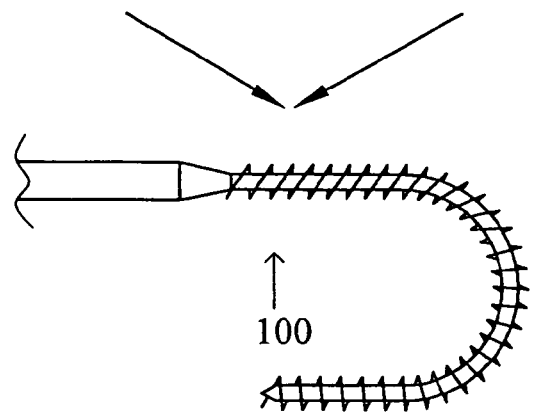
Figure 12:
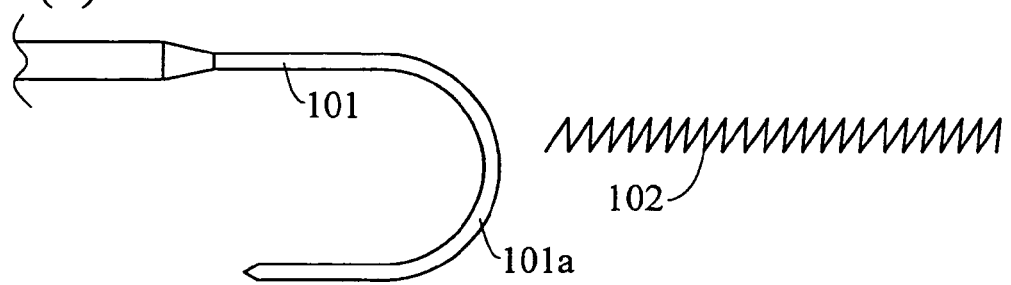
Figure 12:
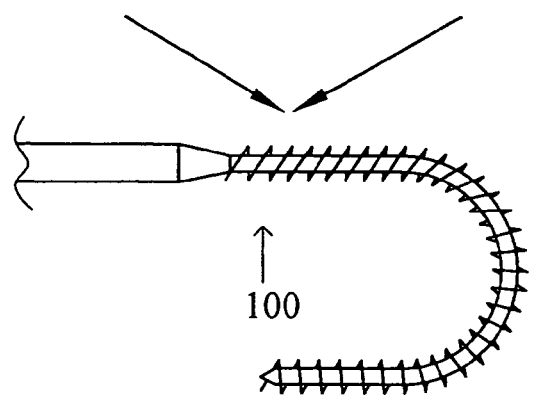
Figure 13:
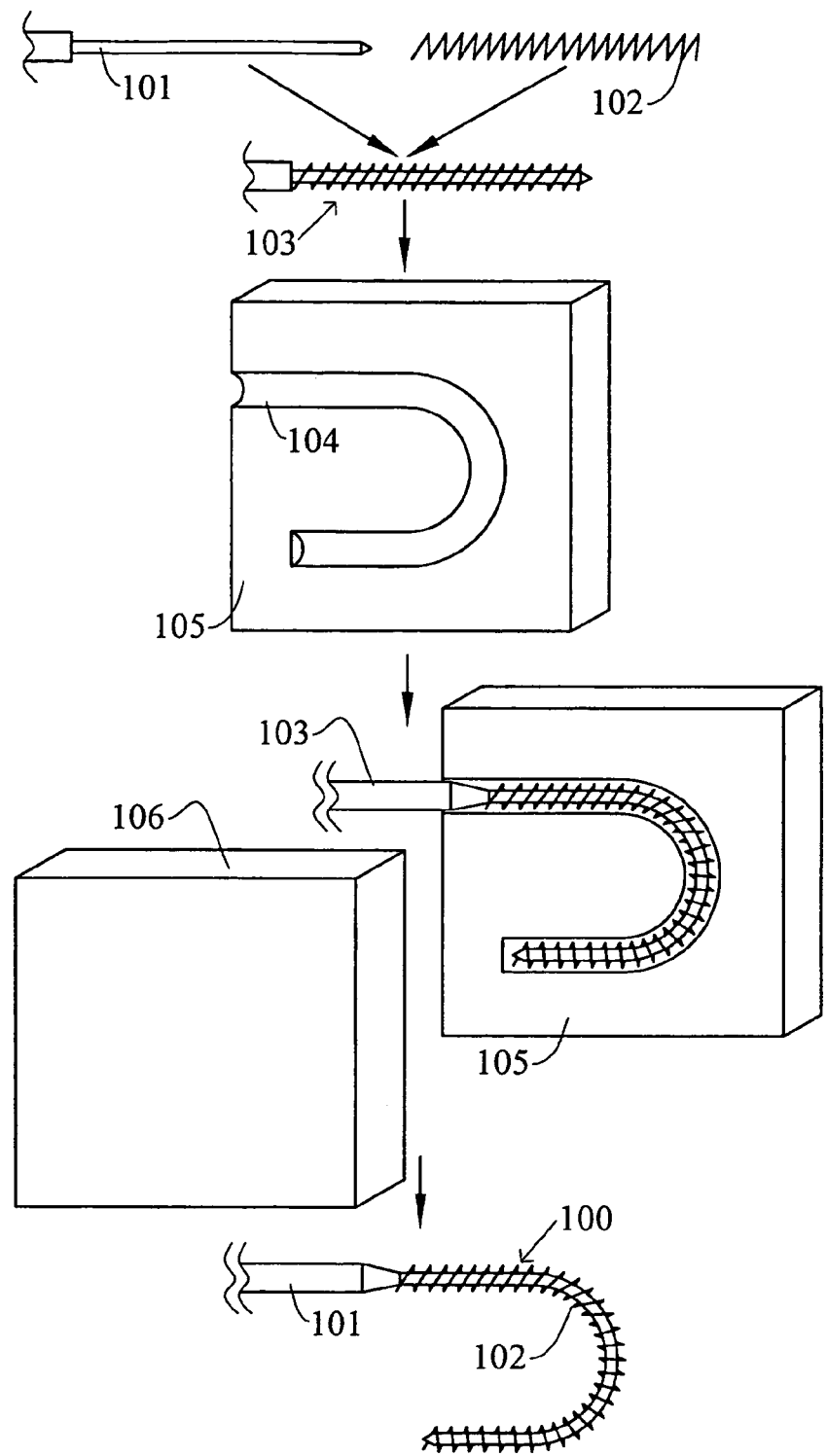
FIG. 13 is a process chart showing the other example of a conventional producing process.

FIG. 10 shows the process chart related to the third aspect of this invention. The process is comprised as follows; the producing step S1 of the coil; the separate producing step S16 of the flat strip plate; the step S17 of rough cutting the flat strip plate; the step S18 of inserting the rough-cut flat strip plate into the coil 16; the step S19 of plasma welding of them at the front end of the coil: the separate producing step S4 of the core wire; the step S15 of J-shaped bending of the front end of the core wire and folding the back end; the step S6 of heat-treating the core wire; the step S7 of removing oxide skin or films; the step S8 of inserting the obtained core wire into the coil obtained by the front-end plasma welding S19; the step S20 of soldering the folded part 30 and the body 31; the separate producing step S21 of the tube; and the step S22 of covering the folded part with the tube to make the handgrip.

Each process is described bellow in detail. The overlapping descriptions with the above description are abbreviated. As shown in left side of FIG. 10, the flat strip plate which is produced in the step S16 and cut in desired length in the rough cutting step S17 is inserted into the coil (step S7) obtained in the step S1. The front ends are plasma-welded (step S18) each other. As shown in right side of FIG. 10, the core wire is produced (step S4). The front end the core wire is curved to shape J, the back end of which is curved to fold back (step S15), and it is heat-treated (step S6). The condition for the heat-treatment is about the same as the embodiment of the core wire described above. After the heat-treatment step S6, removal step S7 of oxide skin or films comes next. This process is the same as described above. In the case that the accuracy after the heat-treatment is high because of the material or dimensions of the core wire, no die is necessary for the heat-treatment, thereby the required time for the temperature rise and the heat release is decreased. No use of the die allows one time heat-treatment of several sets reducing significant required time for the heat-treatment.

The core wire and the coil thus obtained are assembled in the step S8. The front end of the core wire is adjusted to be about 3~8 mm (FIG. 9d) retracted into the coil from the front end of the welded point of the coil 16 and the flat strip plate 26. With this arrangement, since the part 3~8 mm away from the front end has high flexibility always in the up and down direction of the flat strip plate, and moderate rigidity is obtained axially, the front end has both the high flexibility and the buckling strength. The positioning of the front end is carried out when the coil 16 and the core wire 11 are assembled. Keeping the above determined position, the folded part 30 is soldered. In order to induce the solder to flow in the gap between the core wire 11 in the coil 16 and the flat strip plate 26, the pitch of the coil in the soldering part (FIG. 9e) can be made wider.

In the tube producing step S21, the tube for covering the handgrip which is produced in the soldering step S20 is produced. In the step S22 of inserting the resin part, the obtained tube is attached to the handgrip to obtain the complete stiletto 28. After that, dimensional inspections etc. are carried out and packed. The stiletto 28 thus produced has high dimensional accuracy in its flexible front end.

What is claimed is:

1. A process for producing a medical guide wire comprising a core wire having a reduced-diameter portion disposed at a forward end thereof and a coil attached on, wrapped around and in contact with a periphery of the reduced-diameter portion of the core wire, wherein the reduced-diameter portion of the core wire and the coil are heat-treated to shape a desired curved form using a first die for the reduced-diameter portion of the core wire and a second die different from the first die for the coil, and then the shaped coil is attached to the periphery of reduced-diameter portion of the core wire.

2. A process for producing a medical guide wire according to claim 1, wherein the core wire is inserted into the first die being a first tubular die having a first desired curved form and then heat-treated and the coil is inserted in the second die being a second tubular die having a second desired curved form and then heat-treated.

3. A process for producing a medical guide wire according to claim 1, wherein the core wire is inserted into the first die as a die having a first guide groove of a first desired curved form and then heat-treated and the coil is inserted into the second die as a die having a second guide groove of a second desired curved form and then heat-treated.

4. A process for producing a medical guide wire according to claim 1, herein the coil is wound around a periphery of a rod die having a desired outer diameter and then heat-treated.

5. A process for producing a medical guide wire according to claim 1, wherein the heat-treatment is comprised of a 3–200 minutes heating step at the temperature of 80–700° C. and a succeeding heat release step.

6. A process for producing a medical guide wire according to claim 1, wherein the core wire is inserted into the first die being a first tubular die having a first desired curved form and then heat-treated.

7. A process for producing a medical guide wire according to claim 1, wherein the coil is inserted in the second die being a second tubular die having a second desired curved form and then heat-treated.

8. A process for producing a medical guide wire according to claim 1, wherein the core wire is inserted into the first die as a die having a first guide groove of a first desired curved form and then heat-treated.

9. A process for producing a medical guide wire according to claim 1, wherein the coil is inserted into the second die as a die having a second guide groove of a second desired curved form and then heat-treated.

10. A process for producing a medical guide wire comprising a core wire having a reduced-diameter portion disposed at a forward end thereof and a coil attached on, wrapped around and in contact with a periphery of the reduced-diameter portion of the core wire, wherein the reduced-diameter portion of the core wire is inserted into a first tubular die having a desired first curved form and then heat-treated and the coil is inserted into a second tubular die being different from the first tubular die having a desired second curved form and then heat-treated.

11. A process for producing a medical guide wire according to claim 10, wherein the heat-treatment is comprised of a 3–200 minutes heating step at the temperature of 80–700° C. and a succeeding heat release step.

12. A process for producing a medical guide wire comprising a core wire, a coil attached to the periphery of the core wire, and a flat strip plate, wherein the process has following three steps; a first step wherein the flat strip plate is inserted into the coil and an end of the plate is fixed to an end of the coil; a second step wherein the core wire previously heat-treated to shape a desired curved form is inserted into the coil obtained in the first step; and a third step wherein at another end of the coil obtained in the second step, the coil and the flat strip plate are fixed to to each other.

13. A process for producing a medical guide wire according to claim 12, wherein the heat-treatment is comprised of a 3–200 minutes heating step at the temperature of 80–700° C. and a succeeding heat release step.

* * * * *